United States Patent [19]

Voss

[11] Patent Number: 5,764,722
[45] Date of Patent: Jun. 9, 1998

[54] ARRANGEMENT FOR PRODUCING A ROTATING X-RAY BEAM IN A COMPUTED TOMOGRAPHY APPARATUS

[75] Inventor: Gustav Adolf Voss, Hamburg, Germany

[73] Assignee: Siemens Aktiengesellschaft, Munich, Germany

[21] Appl. No.: 837,388

[22] Filed: Apr. 17, 1997

[30] Foreign Application Priority Data

Apr. 29, 1996 [DE] Germany .................. 196 17 131.8

[51] Int. Cl.$^6$ .................................................. G01N 23/00
[52] U.S. Cl. .................................................. 378/10; 378/4
[58] Field of Search .................................................. 378/10, 4

[56] References Cited

U.S. PATENT DOCUMENTS 5,491,734  2/1996  Boyd et al. .................. 378/10
5,504,791  4/1996  Hell et al. .

Primary Examiner—Craig E. Church
Attorney, Agent, or Firm—Hill & Simpson

[57] ABSTRACT

An arrangement for producing an x-ray beam in a computed tomography apparatus allows a scanning of the annular anode by the electron beam to ensue without any gap around the entire circumference of the anode. The electron beam is deflected by kick magnets from an injection circle onto a working circle and, proceeding from the working circle, onto the annular anode for causing an x-ray beam to be emitted from the anode as the point of incidence of the electron beam on the anode moves around the anode circumference.

2 Claims, 2 Drawing Sheets

1

ARRANGEMENT FOR PRODUCING A ROTATING X-RAY BEAM IN A COMPUTED TOMOGRAPHY APPARATUS

BACKGROUND OF THE INVENTION

The present invention is directed to an arrangement for producing an x-ray beam in a computed tomography apparatus of the type having an annular x-radiation source that surrounds a measuring field and in which an annular anode is arranged that is scanned by an electron beam so as to produce a rotating x-ray beam.

The examination of organs or body sections is possible in an extremely short time using an x-ray computed tomography apparatus of this type. The image quality is optimum when the anode is scanned without any gap around the entire circumference of 360°.

SUMMARY OF THE INVENTION

An object of the present invention is to provide an arrangement for producing an x-ray beam in a computed tomography apparatus of the above type wherein a gap-free scanning of the anode around the entire circumference is enabled with a simple structure.

The above object is achieved in accordance with the principles of the present invention in a computed tomography apparatus having an annular x-ray source which surrounds a measuring field, the annular x-ray source including an annular anode which is scanned by an electron beam generated by an electron gun, and which is made to strike the annular anode at a point of incidence which rotates around the measuring field, and having first and second kick magnets which deflect the electron beam from an injection circle to a working circle, with the deflection of the electron beam onto the annular anode ensuing from the working circle. The electron beam can thus be scanned around the entire 360° of the circumference of the annular anode without any gap.

DESCRIPTION OF THE PREFERRED EMBODIMENTS

Figure 1:
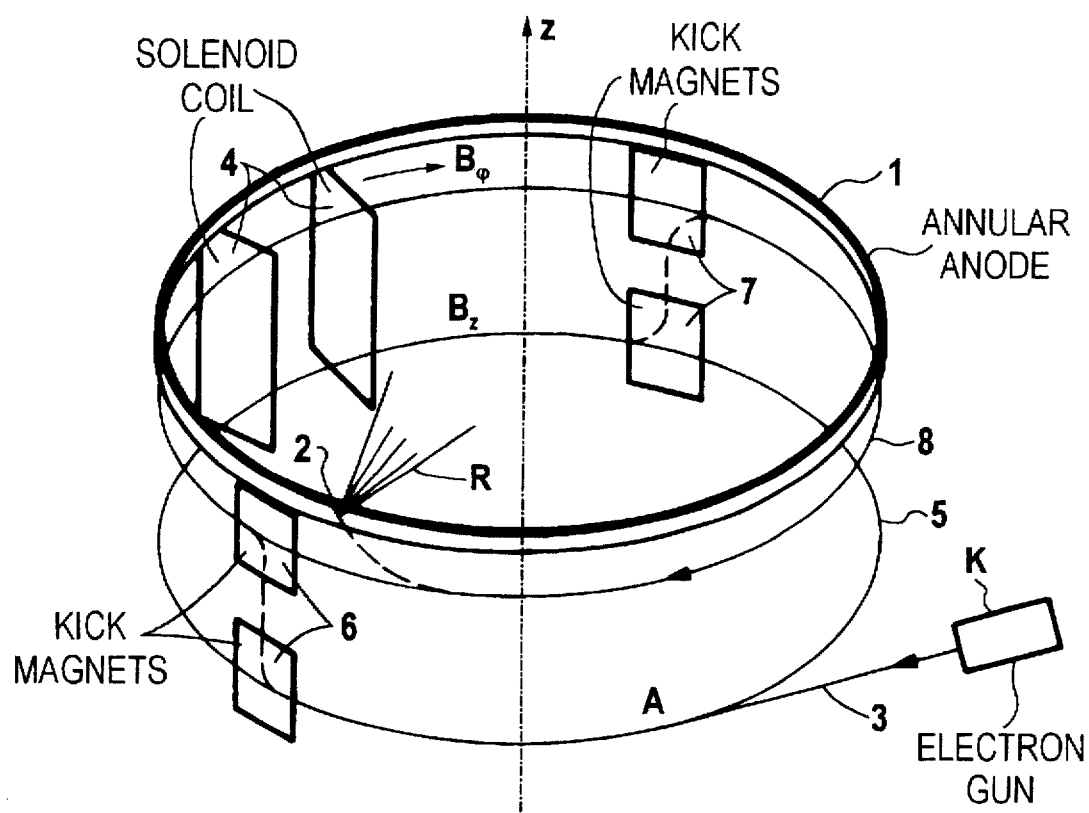
FIG. 1 schematically illustrates the basic components of a computed tomography apparatus of the invention.

FIG. 1 shows the annular anode 1 of a computed tomography apparatus on which a focus 2 circulates from which an x-ray beam R is radially emitted. The focus 2 is the point of incidence of an electron beam 3 that is injected by an electron gun K and that is circularly guided by an annular solenoid coil 4 with a rectangular cross-section, which generates a magnetic field $B_4$ (FIG. 1 shows two cross-section planes) and an additional, axial magnetic field $B_z$. The electron beam 3 is thereby first guided on an injection circle 5 out of which it can be deflected onto a working circle 8 by kick magnets 6 and 7. The deflection onto the annular anode 1 then ensues with further coils that are not shown.

The injection of electrons onto the working circle 8 ensues by means of the kick magnets 6 and 7 that form two transfer shots. That shot that is not located in the ejection region on the working circle 8 at the moment is used in order to avoid disturbances of the ejection by the injection. The electrons located in the working circle 8 can be axially deflected onto the anode 1 gap-free.

The beam transfer between the injection circle 5 and the working circle 8 occurs with fast, pulsed transfer magnets that form the kick magnets 6 and 7 and that are respectively shut off during half the time for the beam transfer. These magnets are designed such that an electron-optical matching between working circle 8 and injection circle 5 is achieved.

Figure 2:
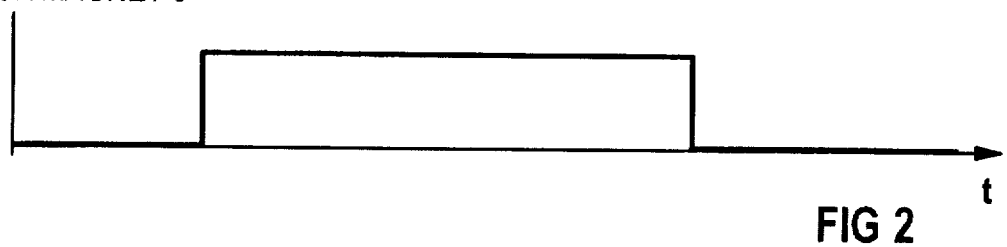
FIG. 2 shows the time curve for the current in one of the kick magnets in the tomography apparatus of FIG. 1.
Figure 3:
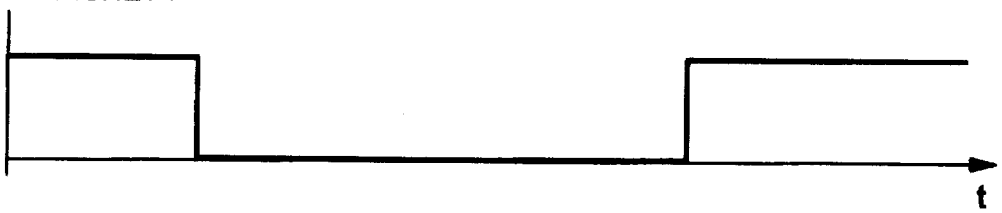
FIG. 3 shows the time curve of the current in the other of the kick magnets in the tomography apparatus of FIG. 1.
Figure 4:
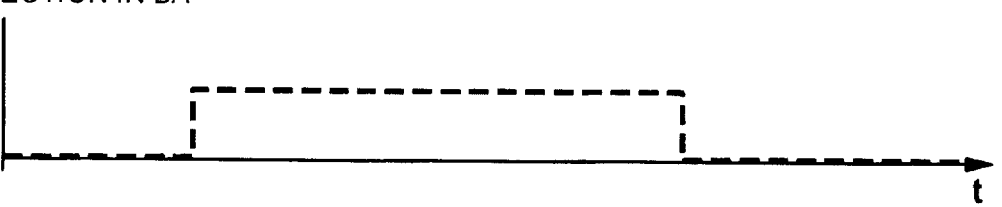
FIG. 4 shows the time curve for the ejection of electrons in a first region of the tomography apparatus of FIG. 1.
Figure 5:
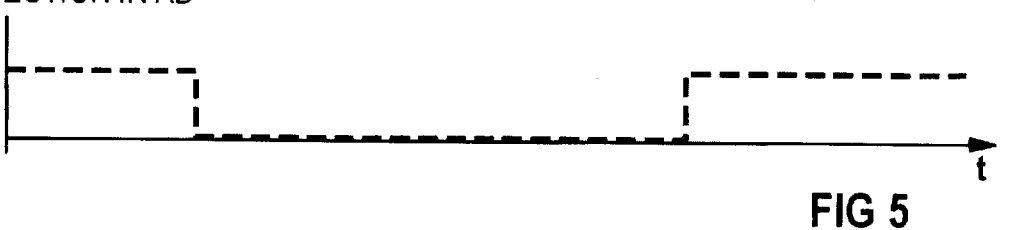
FIG. 5 shows the time curve for the ejection of electrons in a second region of the tomography apparatus of FIG. 1.

FIG. 2 shows the time curve of the current in the kick magnet 6, whereas FIG. 3 shows the time curve of the current in the kick magnet 7. The time curve of the ejection in the region BA is shown in FIG. 4 and in the region AB in FIG. 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. An arrangement for producing a rotating x-ray beam in a computed tomography apparatus, said arrangement comprising:

an electron gun which emits an electron beam;

an annular anode surrounding a measuring field;

first magnet means for guiding said electron beam in a first circle having a circumference, said electron beam propagating completely around said circumference of said first circle, and for guiding said electron beam around a second circle having a circumference, said electron beam propagating completely around said circumference of said second circle;

second magnet means for deflecting said electron beam from said first circle into said second circle; and means for deflecting said electron beam from said second circle onto said anode at a point of incidence on said annular anode which rotates completely around said measuring field for producing an x-ray beam, emanating from said point of incidence, which also completely rotates around said measuring field.

2. An arrangement as claimed in claim 1 wherein said second magnet means comprises a first set of first and second magnets respectively located adjacent said first second circle, and a second set of first and second magnets respectively located adjacent said first circle and said second circle.

* * * * *